United States Patent

Dolan et al.

Patent Number: 5,566,691
Date of Patent: Oct. 22, 1996

[54] FLOSSING APPARATUS

[75] Inventors: John W. Dolan, Boothwyn, Pa.; John W. Spencer, Jr., Rising Sun; Richard Wilson, North East, both of Md.; James Walter, Flagstaff, Ariz.

[73] Assignee: W. L. Gore & Associates, Inc., Newark, Del.

[21] Appl. No.: 481,742

[22] Filed: Jun. 7, 1995

[51] Int. Cl.$^6$ ................................................ A61C 15/00
[52] U.S. Cl. .......................... 132/321; 132/309; 132/323
[58] Field of Search .................................. 132/321, 309, 132/223

[56] References Cited

U.S. PATENT DOCUMENTS

| | | | |
|---|---|---|---|
| 3,744,499 | 7/1973 | Wells. | |
| 3,930,059 | 12/1975 | Wells | 132/321 |
| 4,008,727 | 2/1977 | Thornton | 132/321 |
| 4,011,658 | 3/1977 | Tarrson et al.. | |
| 4,280,500 | 7/1981 | Ono. | |
| 4,450,849 | 5/1984 | Cerceo et al.. | |
| 4,693,365 | 9/1987 | Corella | 206/63.3 |
| 4,832,063 | 5/1989 | Smole. | |
| 4,985,296 | 1/1991 | Mortimer, Jr.. | |
| 4,996,056 | 2/1991 | Blass | 132/321 |
| 5,033,488 | 6/1991 | Curtis et al. | 132/321 |
| 5,220,932 | 6/1993 | Blass | 132/321 |
| 5,320,117 | 6/1994 | Lazzara et al.. | |

Primary Examiner—Nicholas D. Lucchesi
Assistant Examiner—Pedro Philogene
Attorney, Agent, or Firm—Victor M. Genco, Jr.

[57] ABSTRACT

An article is provided for facilitating oral prophylaxis. The article comprises a continuous, elongated fiber of polytetrafluoroethylene having at least one substantially rigid first portion and a substantially flexible second portion comprised of expanded polytetrafluoroethylene.

15 Claims, 2 Drawing Sheets

FLOSSING APPARATUS

FIELD OF THE INVENTION

The present invention relates to oral hygiene, and particularly to an improved integrated dental floss for facilitating oral prophylaxis especially for use with implanted metal abutments, such as fixed orthodontic appliances, or bridges.

BACKGROUND OF THE INVENTION

It is well understood that dental floss use is an important part of a total oral hygiene program. Although toothbrush use helps reduce plaque on the occlusal surfaces of the teeth, floss use reduces plaque accumulation in the interstitial surfaces of the teeth. Caries will develop on surfaces where there is an accumulation of plaque. Dental floss is the only effective means to disrupt the accumulation of plaque in the interstitial regions of the teeth, thereby reducing the likelihood for the development of caries on tooth surfaces. Accordingly, flossing teeth helps prevent periodontal diseases, such as gingivitis.

Since the development of the invention of U.S. Pat. No. 3,953,566 to Gore, flexible fibers made from expanded polytetrafluoroethylene (PTFE) have been used for a variety of purposes, such as for dental floss to clean between teeth. U.S. Pat. No. 4,776,358 to Lorch discloses one such use of an expanded PTFE floss material whereby the floss is folded upon itself to contain active agents. Use of a microcrystalline wax coated expanded PTFE fiber is described in a number of other patents, including U.S. Pat. No. 5,033,488 and U.S. Pat. No. 5,209,251 to Curtis et al. U.S. Pat. No. 5,220,932 to Blass discloses use of a non-porous PTFE floss material. Presently there are a number of commercially available expanded PTFE flosses, including those sold under the trademarks GLIDE® by W. L. Gore & Associates, Inc., COLGATE PRECISION® by Colgate Palmolive Company, and EASY-SLIDE by Johnson & Johnson Consumer Products, Inc.

Expanded PTFE flosses have a number of advantages over conventional nylon flosses, including, but not limited to, resistance to shredding (and its accompanying sticking of fiber shreds between teeth) and high lubricity.

Unfortunately, persons having fixed orthodontic appliances (e.g. braces) or implanted metal abutments (e.g. bridges) have not been able to benefit from the laudable attributes of expanded PTFE flosses without the aid of cumbersome apparatus. More particularly, standard flossing techniques are not appropriate for persons having orthodontic appliances or implanted metal abutments because these devices prevent the floss from freely entering into the interstitial regions in a conventional manner. In the past, devices such as a floss threader or needle have been employed to enable flossing in these instances.

One such threading device is disclosed in U.S. Pat. No. 4,011,658 to Tarrson et. al. This threading device comprises a length of flexible material formed into a loop, the ends of which are bonded together over a substantial portion to provide a stiffened elongated guide portion. Dental floss is threaded through the loop. Thereafter, the threading device, with the guide portion leading, is passed through a desired interstitial region of an area to be flossed. A shortcoming of such a floss threading device is that it is relatively cumbersome to use, especially for persons lacking good dexterity, such as the elderly or handicapped. More particularly, the user of such a flossing apparatus must thread the device prior to the flossing operation. This act of threading the device is similar to that of threading a sewing needle with thread. Such an activity is difficult for persons lacking excellent eyesight or dexterity. Another shortcoming of such a floss threading device is the potential for the device to be swallowed during use if the device becomes separated from the leader floss by unthreading of the two units. In this regard, children may lack the motor skills to remove from their mouth the separated floss threader.

Another flossing apparatus designed to facilitate the flossing of tooth structures and osseous implanted abutments is disclosed in U.S. Pat. No. 4,832,063 to Smole. This device comprises a leader with an affixed cord. Vinyl cement is used to bond the leader to the cord. This bond may fail during use of the apparatus.

In U.S. Pat. No. 3,744,499 to Wells and U.S. Pat. No. 5,320,117 to Lazzara et. al, a dental floss is provided having predetermined stiff portions for use as a pick or leader, and predetermined flexible portions to be used as a dental floss. The stiffening of the dental floss is accomplished by coating the dental floss with a molten thermoplastic or heavy wax. Although this method may have operated with varying degrees of success for floss materials consisting of thermoplastics, such as nylon or polyethylene, or of natural fibers, such as cotton, this method fails in use with dental floss materials comprised of PTFE or expanded PTFE. More particularly, through the use of conventional methods, molten thermoplastic beads on the surface of PTFE, which thereby prevents the formation of a rigid continuous network of the thermoplastic. The beading of the thermoplastic is due to the PTFE's inherent low surface energy and high hydrophobicity.

The foregoing illustrates limitations known to exist in present dental floss materials. Thus, it is apparent that it would be advantageous to provide an improved dental floss apparatus directed to overcoming one or more of the limitations set forth above. Accordingly, a suitable alternative is provided including features more fully disclosed hereinafter.

SUMMARY OF THE INVENTION

In one aspect of the present invention an article is provided for facilitating oral prophylaxis. The article comprises a continuous, elongated fiber of polytetrafluoroethylene having at least one substantially rigid first portion and a substantially flexible second portion comprised of expanded polytetrafluoroethylene.

In another aspect of the present invention, the article comprises an elongated fiber of polytetrafluoroethylene having a predetermined length. The fiber length defines predetermined sections of expanded polytetrafluoroethylene and sintered, substantially full density expanded polytetrafluoroethylene, i.e. substantially non-porous expanded polytetrafluoroethylene, which is substantially more rigid than the expanded polytetrafluoroethylene length sections.

In another embodiment of the present invention, a single use kit is provided for facilitating routine oral prophylaxis. The kit comprises an elongated fiber of polytetrafluoroethylene having a predetermined single use length defined by opposed and first and second end portions. The first end portion is substantially more rigid as compared with the second end portion. A package is provided for hermetically sealing the elongated fiber of polytetrafluoroethylene.

It is, therefore, a purpose of the present invention to provide an improved flossing apparatus comprised of a PTFE material which facilitates oral prophylaxis especially for use with implanted metal abutments, such as fixed orthodontic appliances, or bridges.

Another purpose of the present invention is to provide an improved PTFE dental floss having predetermined stiff portions which may be used as a pick or as a leader, and predetermined flexible portions which may be used as a dental floss.

Another purpose of the present invention is to provide a method for stiffening predetermined portions of a dental floss material made entirely of PTFE.

Another purpose of the present invention is to provide a method to make rigid an expanded PTFE floss apparatus. The expanded PTFE matrix can be filled with a thermoplastic material which is chosen over a thermosetting resin or plastic because the filler material will be co-manufactured with the expanded PTFE material. In this process, heat is required such that a thermosetting resin or plastic material will prematurely set or harden irreversibly. A thermoplastic material, such as nylon, fluorinated ethylenepropylene (FEP) or polyamide, for example, exhibits reversible melt.

Still another purpose of the present invention is to provide a dental floss apparatus made of PTFE, or a form of PTFE, which can be placed easily in the interstitial regions of a user's mouth having implanted metal abutments, or other orthodontic appliances, without requiring cumbersome and potentially hazardous secondary threader devices.

These and other purposes of the present invention will become evident from review of the following specification.

BRIEF DESCRIPTION OF THE DRAWINGS

The foregoing summary, as well as the following detailed description of a preferred embodiment of the invention, will be better understood when read in conjunction with the appended drawings. For purposes of illustrating the invention, there is shown in the drawings an embodiment which is presently preferred. It should be understood, however, that the invention is not limited to the precise arrangement and instrumentality shown. In the drawings.

DETAILED DESCRIPTION OF THE INVENTION

Figure 1:
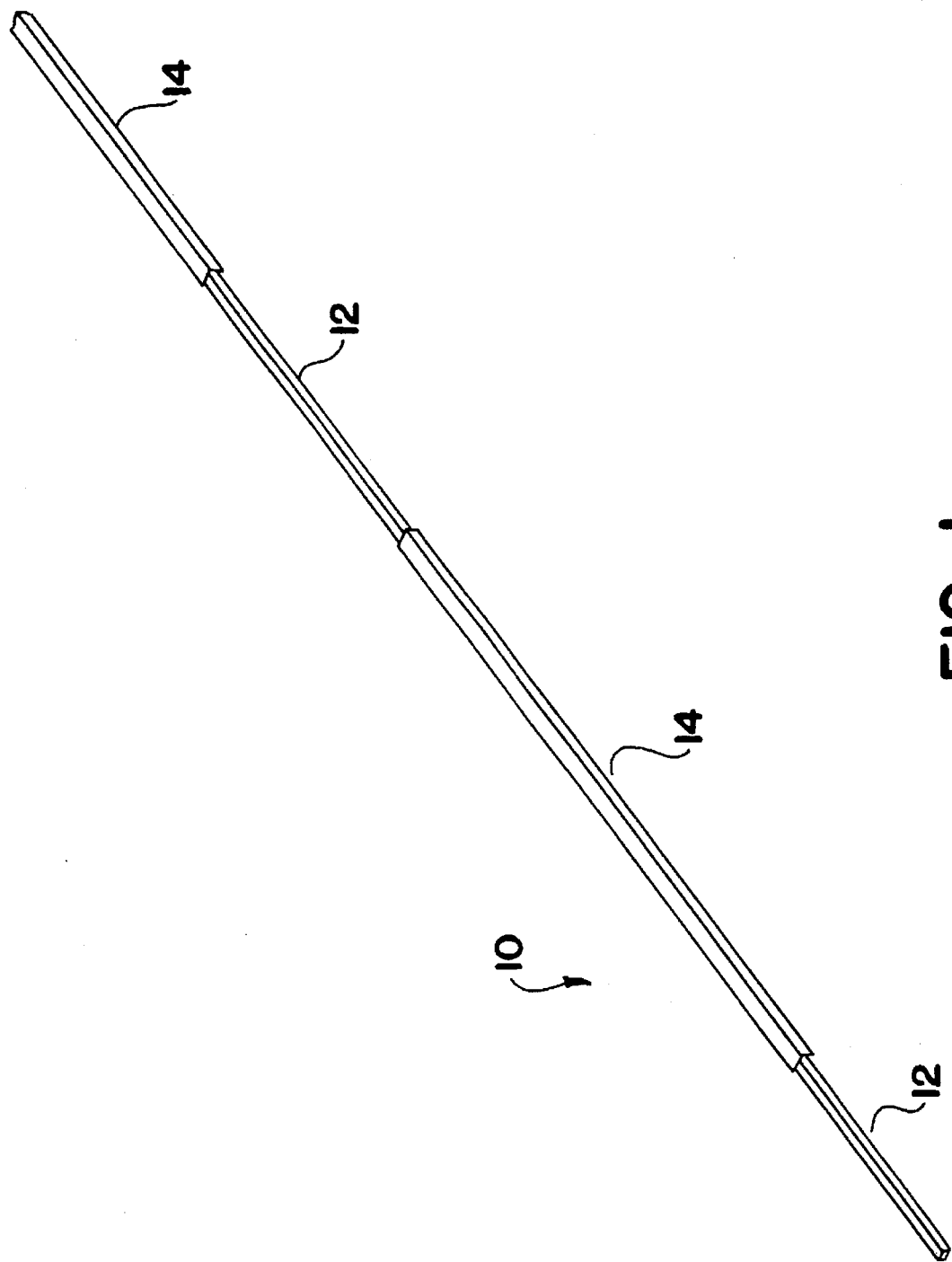
FIG. 1 is an isometric view of an integrated dental floss threader of the present invention.

Referring now to the drawings, the improved floss apparatus of the present invention is generally illustrated at 10 in FIG. 1. The improved floss apparatus comprises a PTFE floss material which includes at least one predetermined stiff or rigid portion 12 and at least one predetermined flexible portion 14. The floss apparatus 10 may be rolled, or otherwise disposed on a bobbin-like apparatus, and may be placed on a supporting core so that it may be easily integrated within a suitable dispensing apparatus (not shown). Alternatively, the floss apparatus may be defined by a single use length which includes a single rigid portion 12 and a single flexible portion 14; such a floss apparatus may be packaged in a single use sterile package.

As the term "floss" is used herein, it is intended to encompass a thread-like material suitable for facilitating oral prophylaxis. Although the description of the present invention focuses upon the use of this novel apparatus as an improved dental flossing apparatus, it is contemplated that this apparatus may provide an excellent improved suture for use in various surgical applications. Accordingly, such use as an improved suture material is fully contemplated within the scope of the present invention.

The apparatus of the present invention comprises a strand of polytetrafluoroethylene (PTFE) fiber material that is essentially rectangular to oblong in cross-sectional dimensions, and which includes at least one predetermined stiff or rigid portion 12 and at least one predetermined flexible portion 14. The fiber may be formed with or without folds. In a folded embodiment, prior to folding, the PTFE fiber has typical dimensions of about 40 µm in thickness and about 2 mm in width. When this material is folded and packaged as dental floss, the material typically has dimensions of about 90 µm in thickness and about 1.2 mm in width. In an unfolded embodiment of the present invention, the PTFE fiber material forms essentially a rectangular to oblong cross-sectional dimension having typical dimensions of about 50 to 250 µm, and preferably 75 to 150 µm, in thickness and about 0.5 to 3 mm, and preferably 0.7 to 1.5 mm, in width. The substantial thickness of this material allows the floss to function extremely well without need for folding or otherwise bulking the height of the material.

The PTFE fiber material may be formed as taught in U.S. Pat. No. 3,543,566 to Gore, incorporated by reference. The preferred sheet comprises a thickness of about 0.5 to 1.0 mm; a density of about 0.8 to 1.5 g/cc; and a tenacity of about 0.5 to 1.0 g/tex.

Each of these properties is measured in a conventional manner. Width and thickness is determined through any conventional means, such as through the use of calipers or through measurements through a scanning electron microscope. Density is determined by dividing the measured weight of the sample by the computed volume of the sample. The volume is computed by multiplying the measured length, width, and thickness of the sample. Tenacity is calculated by dividing the sample's tensile strength by its normalized weight per unit length (tex [grams/1000 meters] or denier [grams/9000 meters]).

This sheet may then be slit into strands by passing the sheet through a series of gapped blades set 0.5 to 20 mm apart. After cutting, the fibers may be subjected to a further heat treatment and/or expansion step, such as through the processes discussed below. Finally, the fibers should be wound onto a spool with care taken to avoid rolling or folding of the fibers during the spooling process.

Preferably, an expanded PTFE sheet is formed and slit into fibers of the present invention in the following manner. A fine powder PTFE resin is blended with a lubricant, such as odorless mineral spirits, until a compound is formed. The volume of lubricant used should be sufficient to lubricate the primary particles of the PTFE resin so to minimize the potential of the shearing of the particles prior to extruding.

The compound is then compressed into a billet and extruded, such as through a ram type extruder, to form a coherent extrudate. A reduction ratio of about 30:1 to 300:1 may be used (i.e., reduction ratio=cross-sectional area of extrusion cylinder divided by the cross-sectional area of the extrusion die). For most applications a reduction ratio of 75:1 to 100:1 is preferred.

The lubricant may then be removed, such as through volatilization, and the dry coherent extrudate expanded in at least one direction about 1.1 to 50 times its original length (with about 1.5 to 2.5 times being preferred). Expansion may be accomplished by passing the dry coherent extrudate over a series of rotating heated rollers or heated plates.

Once this sheet is formed, the sheet may be formed into a fiber by slitting the dry coherent expanded extrudate into predetermined widths by passing it between a set of gapped blades or other cutting means. Following cutting, the slit coherent extrudate may then be further expanded in the longitudinal direction at a ratio of 1:1.1 to 50:1 (with 15:1 to 35:1 being preferred) to form a fiber. Finally, this fiber may be subjected to an amorphous locking step by exposing the fiber to a temperature in excess of 342° C.

The width of the fiber can be controlled by several process variables known in the art of expanding PTFE. Variables which can affect the width of the fiber are: slit width, expansion temperatures and expansion ratio.

The final dimensions of a suitable PTFE fiber material may comprise: a width of about 0.5 to 3.0 mm; a thickness of about 50 to 250 μm; a weight/length of about 80 to 450 tex; a density of about 1.0 to 1.9 g/cc; a tensile strength of about 1.5 to 15 kg; and a tenacity of about 10 to 40 g/tex.

Again, these measurements were made in a conventional manner. Bulk tensile strength was measured by a tensile tester, such as an INSTRON Machine of Canton, Mass. In the case of sheet goods, the INSTRON machine was outfitted with clamping jaws which are suitable for securing the sheet goods during the measurement of tensile loading. The cross-head speed of the tensile tester was 25.4 cm per minute. The gauge length was 10.2 cm. In the case of fibers, the INSTRON machine was outfitted with fiber (horn type) jaws that are suitable for securing fibers and strand goods during the measurement of tensile loading. The cross-head speed of the tensile tester was 25.4 cm per minute. The gauge length was 25.4 cm.

Figure 2:
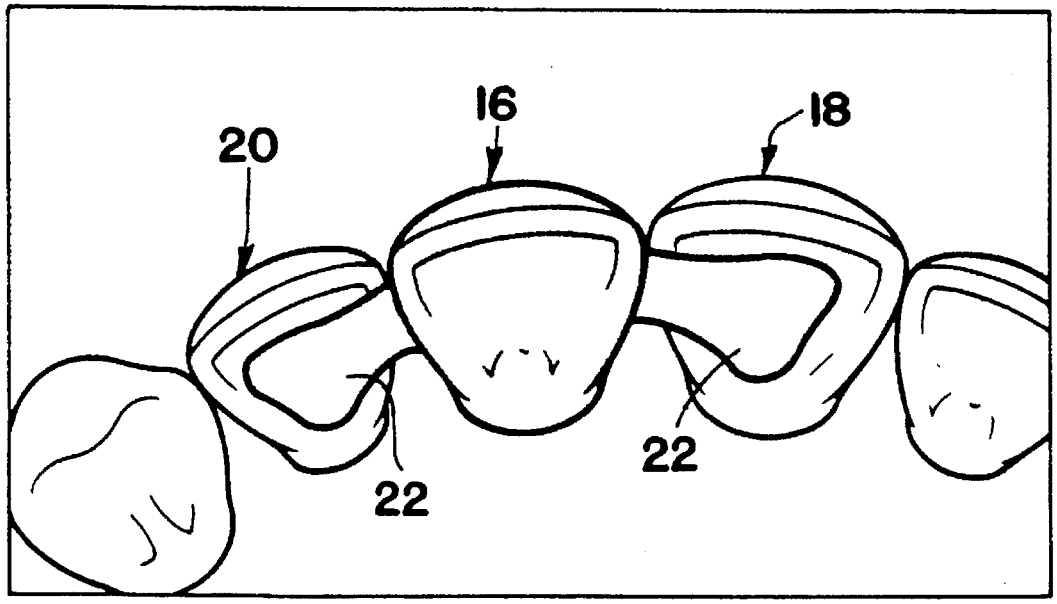
FIG. 2 is an isometric view of a Maryland bridge.
Figure 3:
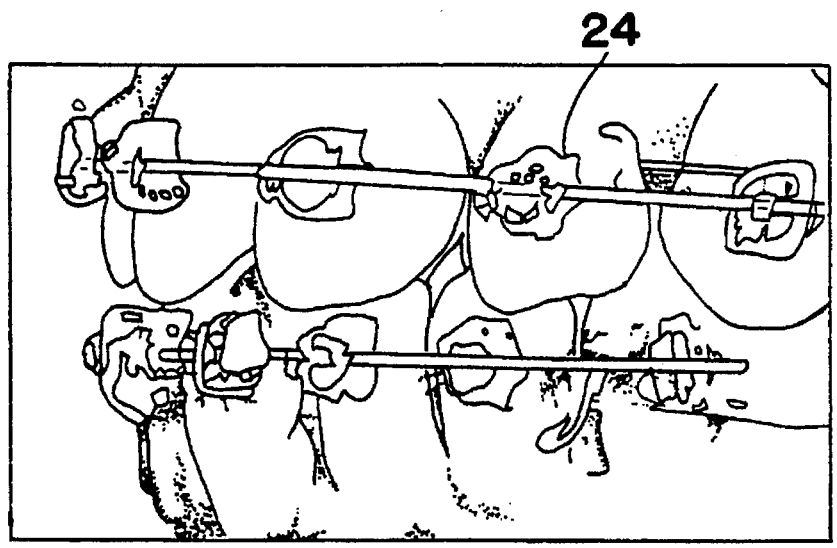
FIG. 3 is a view of a fixed orthodontic appliance.

As best illustrated by FIG. 2, a typical bridge comprises a pontic or false tooth 16, which is anchored by natural teeth 18 and 20 by way of metal supports 22. The stiff or rigid portion 12 facilitates insertion of the apparatus 10 between the teeth, preferably at the gum line, thereby acting as a leader for the flexible portion 14. As best illustrated by FIG. 3, the stiff or rigid portion 12 also facilitates insertion of the apparatus 10 between the interstitial regions of teeth in cases where the person has fixed orthodontic appliances, such as braces 24.

In one embodiment of the present invention, the improved dental floss apparatus 10 is defined by rigid portions 12 comprised of full density PTFE and flexible portions 14 comprised of expanded PTFE. As used herein the term expanded PTFE means a porous PTFE material having a microstructure defined by nodes interconnected by fibrils. This embodiment of the present invention may be made by either selectively expanding predetermined portions of a PTFE fiber, and/or selectively sintering predetermined portions of an expanded PTFE fiber.

The rigid portion 12 may also be formed by performing selective heat relaxation techniques to a fiber of expanded PTFE. By using this method, sufficient heat is applied to the fiber which causes the node and fibril structure of the PTFE to collapse to thereby form substantially rigid portions 12.

In another embodiment of the present invention, the rigid portion 12 is formed by selectively filling predetermined portions of an expanded PTFE fiber with a thermoplastic material, or any other suitable material which would provide rigidity to the expanded PTFE fiber. For example, suitable thermoplastic materials may include, but not limited to, nylon or fluorinated ethylenepropylene.

In yet another embodiment of the present invention, a kit is provided for facilitating routine oral prophylaxis. The kit comprises an elongated fiber of polytetrafluoroethylene having a predetermined single use length defined by opposed and first and second end portions. The first end portion is substantially rigid as compared with the second end portion. The first portion may be comprised of sintered PTFE material, or an expanded PTFE material which has been filled by a suitable material for providing rigidity, such as a thermoplastic material for example. The second portion comprises expanded PTFE. The elongated fiber of polytetrafluoroethylene, having a predetermined single use length, is hermetically sealed in a sterile package.

One method of producing the apparatus 10 with predetermined portions of full density and expanded PTFE may be accomplished by employing induction heating to facilitate the selective expansion and/or the selective sintering of the apparatus 10. As used herein, the term "sintering" means heating the PTFE to at least the crystalline melt point of the PTFE (327° C.).

Induction heating is caused by two mechanisms of energy dissipation, namely, magnetic excitation of ferromagnetic materials and eddy currents which are produced in the material being heated. The magnetic excitation is the repeated re-polarization of magnetic domains in the material being heated in the presence of an alternating current (AC) electrical field emitted by the induction heater coil. The magnetic domains are actually molecules being rubbed together, causing heat from the friction between the moving molecules. The induction heater coil acts as transmitting radio station and the material being heated is the receiving antenna.

The eddy currents in the material being heated are due to the induced voltages produced in the heated material while in the presence of the induction heater electrical field. These eddy currents create heat as they conduct through the material being heated. The tuning of the induction heater to the material being heated is dependent upon the type and size of the material being heated. Generally, the smaller the object to be heated, the higher the required AC operating frequency for the induction heated. Similar to differing antenna lengths for cellular telephones and radios, the electrical "antenna" length of the material to be heated needs to closely match that of the "transmitter," i.e., the induction heater, in order to optimize the coupled energy. Non-metallic materials do not heat when in the presence of the induction heater electrical field, consequently, the option to perform "selective" heating of an assembly processing ferrous and non-ferrous material is possible using induction heating.

With selective or spot expansion/sintering of a PTFE fiber, isolated areas of the PTFE fiber are heated and/or sintered when a metallic article in direct contact with the PTFE fiber is heated by induction. These isolated areas can be heated very quickly to a predetermined temperature above the crystalline melt point of the PTFE, thereby sintering these small areas or zones within the PTFE, which renders the areas or zones unexpandable. The PTFE fiber is then expanded as normal, producing an ePTFE structure of nodes interconnected by fibrils. However, along the fiber length there are defined areas of full density unexpanded PTFE which comprise the rigid portions 12. The transition of these full density, fully sintered areas is very sharp and defined. The shape of the areas or zones is defined by the shape of the metallic metal piece used at the induction heating stage. Multiple spot expansion can be accomplished along the length of a continuous PTFE fiber. In certain instances, a nonconductive heat sink may be needed to keep the heat from transferring down the PTFE fiber and away from the heated zone.

Without intending to limit the scope of the present invention, the apparatus and method of production of the present invention may be better understood by referring to the following examples:

EXAMPLE 1

Fine powder PTFE resin (obtained from the E. I. dupont de Nemours and Company) was blended with about 285 cc of Isopar K, odorless solvent (obtained from the Exxon Corporation) per kg of PTFE resin. The mixture was then compressed into a cylindrical billet, heated to about 50° C. and extruded into a flat sheet of about a 150 mm by 0.7 mm cross sectional dimension in a ram extruder having a reduction ratio of about 70:1. The 0.7 mm thick flat sheet extrudate was stretched in the transverse direction to achieve a width increase of 4.25:1. The extrudate was dried and then cut into 15 cm wide squares. The squares ,were stacked 5 layers high with alternate layers oriented at 90° to each other with respect to their direction of extrusion. The stack was then hot compressed to a thickness of about 1 mm between two flat heated plates to a pressure of about 1000 psi, and to a temperature of about 320° C. The stack was compressed to a density of at least 1.95 g/cc.

A 15 cm by 3.175 mm strip was cut from the sheet of 1 mm material described above. A two piece metal die was placed onto the center of the PTFE strip. The two piece die was about 3.5 cm long and when the two pieces were cut together, they formed a channel or slot about 3.175 mm wide 1.0 mm tall, and 3.5 cm long. An induction heater was provided (Lepel Model #LSS-25). The PTFE material with the die was placed into the induction heater coil. The heater was then turned on for 20 seconds at power setting of 7.0. At the end of the 20 second heat cycle, the ends of the PTFE were pulled thereby expanding the portion of the PTFE within the heated die only, resulting in an article of PTFE that has an area of expansion incorporated between two areas of rigid full density material. The area of expansion had a density of less than 1.90 g/cc.

EXAMPLE 2

A 15 cm by 3.175 mm strip was cut from the PTFE material described in Example 1. The metal die also described in Example 1 was placed in the center of the PTFE strip. The PTFE material with die was placed into the induction heater coil, and the induction heater was turned on for one minute at a power setting of 8.0. At the end of the one minute heating cycle, the metal die and material were removed from the coil and allowed to cool. The metal die was then removed. The PTFE within the die had been sintered. The PTFE strip was then heated to a temperature of about 275° C. and expanded 3:1 longitudinally at a rate of about 10 cm/sec, resulting in an article of PTFE that has a rigid, fully sintered, full density area incorporated within two areas of expanded, porous PTFE.

EXAMPLE 3

A 50-mm portion of a 450-mm piece of 1150 denier (grams/9000 meters) filament of expanded PTFE having a density of 1.8 grams/cc was subjected to heat of a temperature of at least 327 degrees C., but not more than 450 degrees C., for not greater than 5 minutes while under a compressive load of 13.8-MPa using a carver press available from the Fred Carver Company.

The 50-mm compressed portion density was increased to greater than 2 grams/cc and was substantially more rigid than the noncompressed section.

EXAMPLE 4

An aqueous PTFE dispersion, 12% solids polytetrafluoroethylene, was obtained from ICI Americas Co, Wilmington, Del. A nylon micropowder, (type 2001 UD NAT 1, ORGASOL, average particle size of 5 micrometers) was obtained from Elf Atochem North America, Inc, Philadelphia, Pa. A slurry consisting of 20% by weight of nylon micropowder type 2001 UD NAT 1 to solid weight of PTFE found in an aqueous dispersion of approximately 12% solids of polytetrafluoroethylene was created in a 15 liter mixing vessel. 2 parts of Isopropanol to one part nylon by weight was added to the slurry. The total slurry volume was approximately 87,000 cc.

The slurry was mixed until total co-coagulation occurred (approximately 2 minutes) using a 3-blade impeller which consists of two-127 mm blades and one-76 mm blade manufactured by the Lightening Company. The impeller rotated at approximately 120 RPMs.

The coagulum was placed on five 914 mm by 914 mm square stainless steel perforated sheets and then placed in a force air electric oven at 140° C. for a period of 24 hours for drying. The material dried into small, cracked cakes approximately 2 cm thick. The cakes were removed from the five sheets and placed in a clear polyethylene bag and then placed in a freezer to be chilled below 0° C. for a period of at least 24-hours. The polyethylene bag containing the cakes was removed from the freezer and the cakes were immediately ground by passing the chilled cakes by hand through a stainless steel screen which contained 0.635 cm holes using a tight circular motion and minimal downward hand pressure.

The ground particulate was captured in a container and mineral spirits at a concentration of 1.08 cc per gram of powder was added. The powder and liquid mixture was placed in a freezer and chilled for 6 hours allowing for the powder to absorb the mineral spirits.

The mixture was removed from the freezer and immediately passed again through the stainless steel screen containing the 0.635 cm diameter holes using only light hand pressure and in a tight circular motion.

The material was captured in a container; a lid was placed over the container and the material was subjected to a slow tumble cycle lasting for ten minutes.

The material was removed from the closed container and placed in a cylinder. A cylindrical pellet was formed by subjecting the powder in the cylinder to vacuum and an axial pressure of at least 800 psi.

The pellet was then sealed in the tube and heated at 75° C. for at least 6-hours.

The pellet was then extruded through a heated rectangular die having exit-mouth dimensions of 762 micrometers by 153 mm.

The mineral spirits was removed from the extruded tape by running the tape over heated rollers at 165 degrees C. The tape was then stretched in the machine direction at an output speed of 32 meters per minute and an expansion ratio of 2:1. During the expansion operation, the tape was heated to a temperature of approximately 170 degrees C.

The tape was then slit into continuous strips of ribbon 3 mm wide. An optional secondary expansion step may be performed on the ribbon again in order to increase the strength of the material.

The expansion of polytetrafluoroethylene can be readily seen upon review of a differential calorimetry scan of the material over the temperature range of 280° to 385° C. and a scan rate of at least 10 degrees per minute. An endothermic peak occurs during the first heating step at approximately 379° C. which indicates that the material has undergone an expansion operation. Expansion of the polytetrafluoroethylene is desired since the tensile strength of the material increases thus reducing the likelihood of the material breaking in the user's teeth during flossing.

A 450 mm section of the 3 mm wide expanded ribbon is cut from the continuous spool of the ribbon. One distal end approximately 50 mm long is then compressed by placing the 50 mm section in a Carver Press (available from the Fred Carver Company) equipped with upper and lower heated platens set at a temperature of at least 150 degrees C. The 50 mm section was subjected to a compressive load of at least 500 psi for 10 seconds. The resulting structure was a 450 mm long ribbon essentially 3 mm wide having a substantially stiffer section at one distal end approximately 50 mm long and a flexible section integrally connected approximately 400 mm long.

Although a filler content of 20% nylon was used in this example, a filler content ranging from about 0.5% to about 50% thermoplastic material may be appropriate in certain instances to render the expanded PTFE matrix sufficiently rigid especially when coupled with a heated compression step as described above.

EXAMPLE 5

In another method for providing the rigid portions an ultrasonic welding horn equipped with a flat anvil was employed. [The ultrasonic welding unit was model SureWeld 1000 available from SONOBOND Inc., West Chester, Pa. having a nominal output frequency of 35 kHz at 1000 Watts power.] A flat 10 mm diameter horn and a flat 10 mm diameter anvil situated parallel to the horn was used. The gap between the anvil and the horn was set such that maximum oscillation in the horn could be achieved without contact of the two units and without producing undo resonance. The gap was approximately 13 micrometers.

A 50 mm section of the 450 long, 3 mm wide expanded PTFE ribbon was run at a rate of approximately 2.6 meters per second through the energized ultrasonic horn/anvil machine. The ultrasonic unit melted the within the ePTFE material as well as densified the ePTFE matrix. The resulting structure was a 450 mm long ribbon essentially 3 mm wide having a substantially stiffer section at one distal end approximately 50 mm long and a flexible section integrally connected approximately 400 mm long which is suitable for flossing.

The ultrasonic unit can be easily incorporated into a continuous production line to densify the continuous ribbon in select regions, rendering the such select regions substantially stiffer than the region which had not been passed through the ultrasonic unit during the time it was energized. Ribbon produced in such a line can have select densified portions at some periodicity, for example a 50 mm densified portion for every 400 mm of ribbon.

Although a few exemplary embodiments of the present invention have been described in detail above, those skilled in the art readily appreciate that many modifications are possible without materially departing from the novel teachings and advantages which are described herein. Accordingly, all such modifications are intended to be included within the scope of the present invention, as defined by the following claims.

Having described the invention, what is claimed is:

1. An article for facilitating oral prophylaxis comprising:
an elongated fiber of polytetrafluoroethylene having a predetermined length, said fiber length defining at least one section of porous polytetrafluoroethylene and at least one section of substantially non-porous polytetrafluoroethylene which is substantially more rigid than said porous polytetrafluoroethylene length section, wherein the at least one section of substantially non-porous polytetrafluoroethylene has a density of at least 1.95 g/cc.

2. The article of claim 1, wherein the at least one section of porous polytetrafluoroethylene has a density of less than 1.90 g/cc.

3. The article of claim 1, wherein the at least one section of substantially non-porous polytetrafluoroethylene is comprised of an expanded polytetrafluoroethylene which has been filled with a suitable material for providing rigidity.

4. The article of claim 3, wherein the expanded polytetrafluoroethylene is filled with a thermoplastic material.

5. The article of claim 4, wherein the thermoplastic material is nylon.

6. The article of claim 5, wherein the thermoplastic material is fluorinated ethylenepropylene.

7. A single use kit for facilitating routine oral prophylaxis, the kit comprising:
an elongated fiber of polytetrafluoroethylene having a predetermined length, said fiber length defining a first end portion of substantially non-porous polytetrafluoroethylene and a second end portion of porous polytetrafluoroethylene, the first end portion being substantially more rigid than said second end portion; wherein the first end portion of substantially non-porous polytetrafluoroethylene has a density of at least 1.95 g/cc; and
a package for hermetically sealing the elongated fiber of polytetrafluoroethylene.

8. The single use kit of claim 7, wherein the first end portion is comprised of an expanded polytetrafluoroethylene which has been filled by a suitable material for providing rigidity.

9. The single use kit of claim 8, wherein the expanded polytetrafluoroethylene is filled with a thermoplastic material.

10. The single use kit of claim 9, wherein the thermoplastic material is nylon.

11. The single use kit of claim 9, wherein the thermoplastic material is fluorinated ethylenepropylene.

12. A dental floss comprising:
a continuous, elongated fiber of polytetrafluoroethylene, having a thermoplastic filler content ranging from about 0.5% to about 50% thermoplastic material, the elongated fiber defining at least one substantially rigid first portion and at least one substantially flexible second portion, wherein the at least one substantially rigid first portion has a density of at least 1.95 g/cc.

13. The dental floss of claim 12, wherein the at least one substantially flexible second portion section has a density of less than 1.90 g/cc.

14. The dental floss of claim 12, wherein the thermoplastic material is nylon.

15. The dental floss of claim 12, wherein the thermoplastic material is fluorinated ethylenepropylene.

* * * * *